Figure 1:
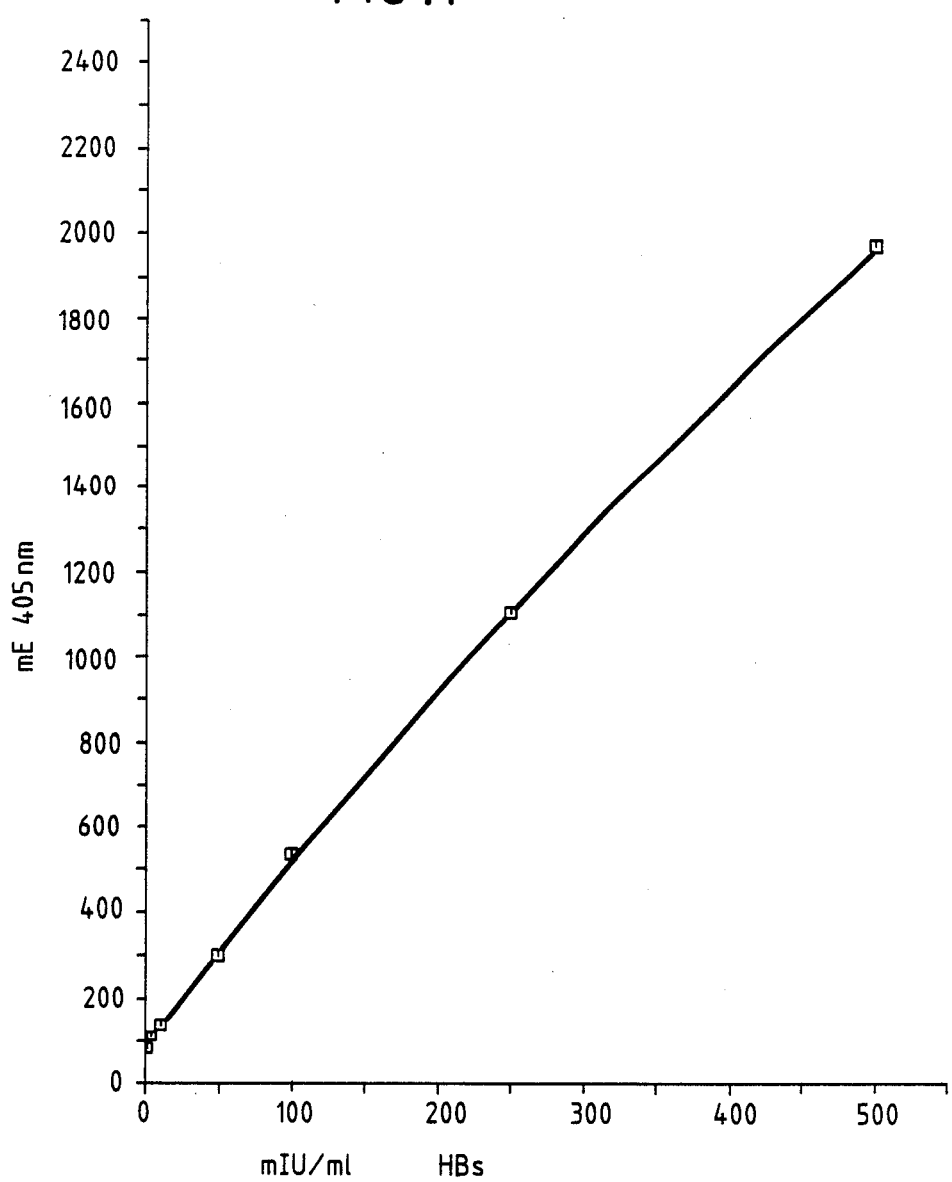

United States Patent [19]

Geiger et al.

[11] Patent Number: 4,945,042
[45] Date of Patent: Jul. 31, 1990

[54] PROCESS AND REAGENT FOR THE DETERMINATION OF AN ANTIBODY

[75] Inventors: Thomas Geiger, Diessen; Wolf D. Engel, Pähl, both of Fed. Rep. of Germany

[73] Assignee: Boehringer Mannheim GmbH, Mannheim, Fed. Rep. of Germany

[21] Appl. No.: 157,707

[22] Filed: Feb. 19, 1988

[30] Foreign Application Priority Data

Feb. 23, 1987 [DE] Fed. Rep. of Germany ....... 3705686

[51] Int. Cl.$^5$ .................. G01N 33/535; G01N 33/53; G01N 33/563; G01N 33/543
[52] U.S. Cl. ......................................... 435/7; 435/805; 435/810; 436/501; 436/504; 436/512; 436/518; 436/538; 436/541; 436/542; 436/827
[58] Field of Search ........................... 435/7, 805, 810; 436/501, 504, 512, 518, 538, 540, 541, 539, 542, 822, 823, 827

[56] References Cited

U.S. PATENT DOCUMENTS 4,778,751  10/1988  El Shami et al. ........................ 435/7

Primary Examiner—Esther M. Kepplinger
Assistant Examiner—Toni R. Scheiner

Attorney, Agent, or Firm—Felfe & Lynch

[57] ABSTRACT

The present invention provides a process for the determination of an antibody by incubation with three different reagents $R_1$, $R_2$ and $R_3$, of which $R_1$ and $R_3$ are present in liquid phase and are bindable with the antibody, $R_2$ is present bound to a solid phase and is bindable with $R_1$ and $R_3$ carries a label, separation of the solid phase from the liquid phase and measurement of the label in the solid phase, wherein as $R_1$ there is used a conjugate of a substance specifically recognized by the antibody to be determined and a reaction component of a specific binding system, as $R_3$ there is used a conjugate of a substance specifically recognized by the antibody to be determined and a label and as $R_2$ there is used the other binding component of the specific binding system.

The present invention also provides a composition for the determination of an antibody, wherein it contains two different soluble reagents $R_1$ and $R_3$ specifically bindable with the antibody, of which $R_1$ carries a reaction component of a specific binding system and $R_3$ carries a label and also a receptor $R_2$ which is present in solid phase and is bindable with the receptor $R_1$, the insoluble receptor $R_2$ and the soluble receptor $R_1$ being present physically separated from one another.

10 Claims, 2 Drawing Sheets

PROCESS AND REAGENT FOR THE DETERMINATION OF AN ANTIBODY

The present invention is concerned with a process and reagent for the determination of antibodies.

More particularly, the present invention is concerned with a process for the determination of an antibody by incubation with three different receptors $R_1$, $R_2$ and $R_3$, of which $R_1$ and $R_3$ are present in liquid phase and are bindable with the antibody, $R_2$ is present in solid phase and is bindable with $R_1$ and $R_3$ carries a label, separation of the solid phase from the liquid phase and measurement of the label in the solid phase.

Antibodies are protein molecules which, after contact with the corresponding antigens, are produced by B-lymphocytes and plasma cells and are specifically directed against the antigens initiating their formation. Therefore, the detection of antibodies against particular antigens can give conclusions with regard to the stage of a disease or to the presence of autoimmune diseases.

Antibodies can be sensitively detected by processes according to the immunoassay principle, various variants here being possible. Thus, for example, the antigen can be covalently bound to a carrier, brought into contact with the solution which contains the antibody to be determined and subsequently reacted with an antibody directed against this antibody, the antibody usually being an anti-Ig-antibody, which is labelled in known manner. The measurement of the bound label then gives a conclusion regarding the amount of the antibody content. It is a disadvantage of this process that falsely positive values are obtained due to nonspecific binding of non-specific antibodies contained in the sample. Furthermore, this determination can only be carried out in two successive steps. A further test for the detection and for the quantitative determination of an antibody consists in that antigens against the antibodies to be determined are fixed on a solid phase. Subsequently, there is added thereto a patient's serum, together with a predetermined amount of the antibody to be determined but which carries a label and subsequently the label bound to the solid phase is measured. It is thus a competitive test, the sensitivity of which leaves something to be desired. A further possibility is to bind an anti-Ig antibody to a solid phase and then to react it with the test solution. Subsequently, there is added an antigen specific for the antibodies to be determined, which antigen carries a label. A disadvantage of this method is the limited binding capacity of the solid phase since, apart from the antibody to be determined, other antibodies of the same globulin class are also bound.

A further variant is to coat a solid phase with the specific antigen of the antibody to be determined, subsequently to react this solid phase with the sample solution and thereafter, in a further step, to add thereto a specifically bindable substance which carries a label. Such processes are known, for example, from European Patent Specifications Nos. 0,168,689 and 0,160,900. A disadvantage of this process is that a different solid phase must be used for each determination since, in each case, the solid phase carries the specific antigen. It is a further disadvantage that the reaction of the antibody with the antigen takes place heterogeneously. Furthermore, two steps are always necessary for processes of this kind. Consequently, however, such processes cannot be transferred to analysers in which only a single washing step can be carried out.

Therefore, it is an object of the present invention to provide a process for the determination of antibodies which can be carried out in one step and with only one single washing step and thus can be automated. Furthermore, it is an object of the present invention to provide a process in which one kind of solid phase can be used for many different tests.

Thus, according to the present invention, there is provided a process for the determination of an antibody by incubation with three different receptors $R_1$, $R_2$ and $R_3$, of which $R_1$ and $R_3$ are present in liquid phase and are bindable with the antibody, $R_2$ is present bound to a solid phase and is bindable with $R_1$ and $R_3$ carries a label, separation of the solid phase from the liquid phase and measurement of the label in the solid phase, wherein as $R_1$ there is used a conjugate of a substance specifically recognised by the antibody to be determined and a reaction component of a specific binding system, as $R_3$ there is used a conjugate of a substance specifically recognised by the antibody to be determined and a label and as $R_2$ there is used the other binding component of the specific binding system.

The process according to the present invention depends upon the principle that two soluble binding components, one of which is a conjugate of a substance which carries at least one epitope specific for the antibody to be determined, for example an antigen, antigen fragment, anti-idiotypical antibody or hapten, with a component of a specific binding system and the other of which is a conjugate of a substance which carries at least one epitope specific for the antibody to be determined, for example an antigen, antigen fragment, anti-idiotypical antibody or hapten, and a label compete for the at least doubly specifically bindable paratope of the antibody to be determined, the following reaction products thereby being formed: antibodies which have bound not only $R_1$ but also $R_3$, antibodies which have only bound $R_1$ and antibodies which have only bound $R_3$. Only the first two reaction products can be bound to the solid phase since they carry a reaction component of the specific binding system. The reaction product in which $R_3$ only is bound is washed out. Since the antibody to which only $R_1$ is bound does not have a label, it does not participate in the measurement. Therefore, the determination of the concentration of the antibody takes place only via the antibody molecules which have bound $R_1$ and $R_3$. The highest sensitivity is thereby achieved when the amount of substance specifically recognised by the antibody to be determined, which is also called immune-reactive, in $R_1$ is greater than or equal to the amount of immune-reactive substance in $R_3$. The immune-reactive substances in $R_1$ and $R_3$ are preferably used in a ratio of 20 to 1:1, a ratio of 5 to 1:1 being especially preferred. The interpretation is possible via the bound, labelled conjugate and, with the help of a calibration curve, the concentration of the antibody in the sample can be determined.

Surprisingly, according to the present invention, it is thus possible to determine antibodies with very great exactitude and in a simple process. The determination process according to the present invention is not disturbed by high concentrations of antibodies which are not to be determined. An especial advantage of the process is the rapidity and simplicity of the assay procedure.

The process according to the present invention can be used for the determination of antibodies of all classes, for example IgG, IgM, IgA, IgD and IgE, as well as mixtures thereof.

Since each of the receptors and also the antibodies to be determined can, in each case, only react specifically with the reaction component intended for it, it is possible to incubate all receptors and the sample together and to carry out the process in one step. This then only requires a single washing step after the incubation. Of course, it is also possible to carry out the process according to the present invention in two steps. In this case, the sample is preferably first incubated with the receptors $R_1$ and $R_3$ and subsequently the complex resulting from $R_1$, $R_3$ and antibody to be determined is added to the solid phase-bound $R_2$. A further advantage of the process according to the present invention is the one-step method of proceeding since it is thereby possible to automate the process in a simple manner.

For carrying out the process according to the present invention, three different receptors $R_1$, $R_2$ and $R_3$ are used. The receptors $R_1$ and $R_3$ are each present in liquid phase and preferably in the same concentration. In each case, they consist of a substance which carries an epitope specific for the antibody to be determined. This substance is, in each case, a conjugate of two parts, one part thereby carrying the epitope and being, for example, an antigen, an antigen fragment, an anti-idiotypical antibody or a hapten. The antibody-specific substances contained in the receptors $R_1$ and $R_3$ can be the same or different. The other part of the conjugate is, in the case of $R_1$, a reaction component of a specific binding system. By a specific binding system is here to be understood two components which can react specifically with one another. The binding ability can thereby depend upon an immunological reaction or, however, on some other specific reaction.

The specific binding system is preferably a combination of biotin and avidin; biotin and streptavidin; biotin and antibiotin; hapten and antihapten; Fc$\gamma$-fragment of an antibody and antibody against this Fc$\gamma$-fragment or carbohydrate and lectin. One of the reaction components of this specifically bindable pair is then a part of the conjugate which forms the receptor $R_1$.

The other reaction component is the receptor $R_2$, which is present in solid phase. The binding of $R_2$ to an insoluble carrier material can be carried out according to the usual, known methods for fixing binding components, preferably biological binding systems, to solid carrier substances. Not only a covalent but also an adsorptive binding can be used. Because of the hereby achievable higher yield and the simplified manner of working, it is preferred to use a solely adsorptive binding, for example on to synthetic resin. Especially preferred as solid phase are reagent test tubes or microtitre plates made of polystyrene and similar synthetic resins which are adsorptively coated on the inner surface with $R_2$. Also preferable are particulate substances, for example molecular sieve materials, small glass bodies, synthetic resin tubes and the like. Especially preferred as a carrier of the solid phase, there is used a porous, laminar carrier, for example paper. As $R_2$, on to the solid phase is fixed the reaction component of the specific binding system.

The receptor $R_3$ also carries, apart from the antigen, antigen fragment or hapten, a label as the other part of the conjugate. The label is preferably an enzyme or a fluorescing, chemiluminescing or radioactive substance.

Processes for labelling antigens, antigen fragments or haptens are well known, for example, from Clin. Chim. Acta, 81, 1–40/1977, and do not here require any further explanation. The label can be determined in known manner.

In a preferred embodiment of the process according to the present invention, the receptors $R_1$ and $R_3$, as well as the sample containing the antibody to be determined, are incubated, $R_1$ and $R_3$ thereby reacting with statistical probability with the paratopes of the antibody to be determined. This reagent mixture is subsequently brought into contact with the solid phase carrying the receptor $R_2$.

The reaction component of the specific binding system contained in $R_1$ reacts with $R_2$. After the incubation, there is carried out a phase separation of the solid phase from the liquid phase, for example by sucking off. After washing the solid phase, the measurement of the label can be carried out and represents a measure for the amount of antibody to be determined. If the label is an enzyme, it is sufficient simply to measure the enzymatic activity in a manner generally known therefor. As enzyme label, it is especially preferred to use peroxidase or $\beta$-galactosidase.

If the label is not carried out with an enzyme but with a radioactive substance, an isotope, a fluorescing or chemiluminescing substance, then the determination is here carried out according to well-known methods.

If the process is carried out in a centrifugal analyser, then it is preferred first to centrifuge the sample over a carrier on which are present the two receptors $R_1$ and $R_3$ in dissolvable form, the receptors $R_1$ and $R_3$ hereby being dissolved. By means of appropriate chronologically arranged stopping phases, there is brought about the dissolving of the receptors $R_1$ and $R_3$ and the complex formation thereof with the antibody to be determined and present in the sample. In the next step, the reaction mixture formed is brought on to the solid phase, where the final reaction then takes place.

It is also possible to bring the receptors $R_1$ and $R_3$ and the sample, without a stopping phase for the complex formation, directly on to the solid phase with the receptor $R_2$. Since the reaction between the receptors $R_1$ and $R_3$ and the antibody to be determined is homogeneous, it takes place much more quickly than the reaction between $R_1$ and $R_2$ on the heterogeneous phase boundary. Therefore, this carrying out of the reaction leads to results which do not differ substantially from those which are obtained when carrying out the reaction with a stopping phase.

In an especially preferred embodiment of the process according to the present invention, all three receptors, as well as the sample containing the antibody to be detected, are incubated, $R_1$ and $R_3$ thereby reacting with statistical probability with the paratopes of the antibody to be determined and the reaction component of the specific binding system contained in $R_1$ reacting with $R_2$. As previously described, here, too, the homogeneous reaction between $R_1$, $R_3$ and the antibody to be determined proceeds substantially more quickly than the heterogeneous reaction between $R_1$ and $R_2$ and is, therefore, not hindered. After the incubation, there is carried out a phase separation of the solid phase from the liquid phase, for example by sucking off. After washing the solid phase, the measurement of the label can be carried out and represents a measure for the amount of antibody to be determined.

In a further embodiment, it is also possible first to bring the sample into contact with the solid phase and then to add thereto the reaction mixture containing the receptors $R_1$ and $R_3$. This process is especially advantageous for automatic analysers which cannot simultaneously dose the sample and reagent.

The present invention also provides a reagent for the determination of an antibody, wherein it contains two different, soluble receptors $R_1$ and $R_3$ bindable with the antibody, of which $R_1$ carries a reaction component of a specific binding system and $R_3$ carries a label and also a receptor $R_2$ which is present in solid phase and is bindable with the receptor $R_1$, the insoluble receptor $R_2$ and the soluble receptor $R_1$ being present physically separated from one another.

Since the receptor $R_3$ reacts neither with $R_1$ nor with $R_2$, its introduction into the reagent is not critical. Preferably, however, $R_1$ and $R_3$ are kept together in the reagent. $R_1$ and $R_3$ are thereby contained together in a liquid or lyophilised reagent. $R_2$ is present separate therefrom, bound to an insoluble carrier material.

In a further embodiment, the receptors $R_1$ and $R_3$ can be present in soluble form and the receptor $R_2$ in insoluble form and separate from $R_1$ in a solid carrier material. As carrier materials, there can be used materials which are inert under the conditions arising in the case of the present invention which are able to fix $R_2$ by chemical or physical binding, such materials being well known in large number. It is preferred to use an absorbing, swellable or soluble film-forming carrier material, for example a carrier material known for test strips, such as paper or similar fleece materials.

Figure 2:
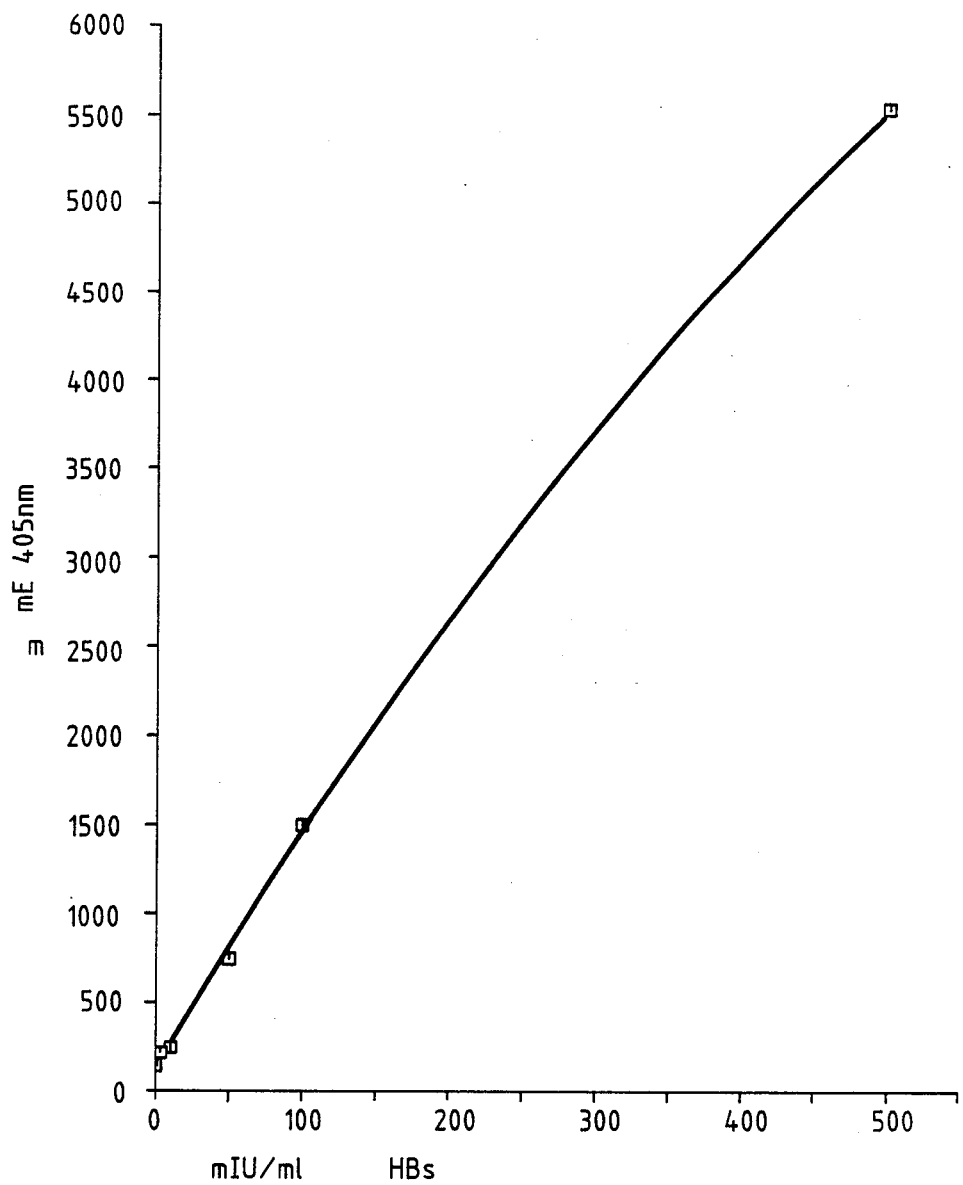

The following Examples and the accompanying drawings are given for the purpose of illustrating the present invention. In the drawings:

FIG. 1 is a calibration curve for the process according to Example 4 with increasing amounts of Hbs antibody; and FIG. 2 is a calibration curve for the process according to Example 5 with increasing amounts of HBs antibody.

EXAMPLE 1.

Preparation of reagent solutions (1) Preparation of an HBsAg-mouse-IgG conjugate (receptor 1).

1a. Limited reduction of HbsAg (hepatitis B-surface antigen.

5 mg. HbsAg (preparation according to J. Virol. Meth., 11, 225–230/1985) in 5 ml. 10 mM sodium acetate buffer (pH 4.5) are brought to 50 mM with dithiothreitol and kept for 30 minutes at 25° C.

1b. Desalination of the reaction batch.

The reaction batch is chromatographed and fractionated over a Sephadex G-25 column (diameter 16 mm., packing height 15 cm.) in 10 mM sodium acetate buffer (pH 4.5) at a flow rate of 40 ml./hour. The fractions with absorbance at 280 nm ($E \geq 0.3$) are pooled and dialysed for 24 hours against 30 mM potassium phosphate buffer (pH 7.1) ($3 \times 1$ liter of dialysis medium).

1c. Modification of IgG (mouse normal IgG, M-n IgG).

To a solution of 10 mg. M-n IgG (produced by Calbiochem GmbH, Frankfurt, Federal Republic of Germany) in 1 ml. 30 mM potassium phosphate buffer (pH 7.1) are added 10 $\mu$l. of a solution of maleinaminohexanoyl-N-hydroxysuccinimide ester (MHS) in dimethyl sulphoxide (14.3 mg. MHS/1 ml. dimethyl sulphoxide) and left to react for 1 hour at 25° C.

1d. Desalination of the modification batch.

The batch from 1c is chromatographed and fractionated over 10 ml. Sephadex G 25 in 30 mM potassium phosphate buffer (pH 7.1) (flow rate 40 ml./hour). The fractions of the protein peak with the highest protein concentration are pooled. These contain the maleinaminohexanoyl-modified M-n IgG-antibody.

1e. Conjugation batch.

To 2 mg. of reduced HBsAg from 1b in 4 ml. 30 mM potassium phosphate buffer (pH 7.1) are added 10 mg. maleinamino-hexanoyl M-n-IgG according to 1d in 1.6 ml. 10 mM potassium phosphate buffer (pH 7.1). After mixing, the batch is allowed to react for 1 hour at 25° C. The reaction is terminated by the addition of cysteine to 1 mM, then left to react for 30 minutes at 25° C., whereafter iodoacetamide is added thereto to 5 mM and allowed to react further for 30 minutes at 25° C. Subsequently, the reaction mixture is concentrated to a concentration of 15 mg./ml.

1f. Chromatographic separation of the conjugate batch.

After concentration to 0.8 ml., the batch is applied to Superose 6 prep (Pharmacia) (about 80 ml.) and chromatographed with a linear flow rate of 5 cm./hour (10 mM potassium phosphate buffer pH 7.5; 0.2% sucrose 0.1% azide). The fractions in the void volume are the desired product.

(2) Sheep anti-mouse-Fc$\gamma$ (receptor 2).

2a. Sheep anti-mouse-Fc$\gamma$ antiserum is purified as follows: A serum containing this antibody is mixed with ammonium sulphate to 1.8M. The precipitate obtained is taken up in 15 mM sodium phosphate buffer (pH 7.0) containing 50 mM sodium chloride. The so obtained solution is subjected to a passage over DEAE-cellulose.

2b. Immunosorptive purification.

The sheep-anti-mouse-Fc$\gamma$ reagent from 2a is passed in PBS buffer (phosphate buffered saline pH 7.5) in the course of 2 hours Spherosil-bound mouse-IgG (about 1 ml. M-IgG-Spherosil per 50 mg. of reagent protein). After washing out the non-bound protein, the specifically bound part is eluted with 1M propionic acid. The product is dialysed and lyophilised.

3. Preparation of an HBsAg-$\beta$Gal conjugate (receptor 3).

3 (a,b) Limited reduction and desalination of HBsAg analogous to 1 (a,b).

3 (c) Modification of $\beta$-galactosidase ($\beta$-Gal).

To a solution of 10 mg. $\beta$-Gal in 1 ml. 30 mM potassium phosphate buffer (pH 7.1) are added 50 $\mu$l. bis-maleimido-methyl ether (BMME) (47 mg. BMME/ml. anhydrous dimethyl sulphoxide), mixed and left to react for 1 hour at room temperature.

3 (d) Desalination of the modified $\beta$-Gal.

The reaction batch from (3c) is cooled to 4° C. and chromatographed and fractionated at this temperature over 10 ml. Sephadex G-25 in 30 mM potassium phosphate buffer (pH 7.1) at a flow rate of 40 ml./hour. The fractions with the highest protein content are pooled (protein concentration 6 mg./ml.): $\beta$-Gal-BMME.

3 (e) Conjugate batch.

To 2 mg. reduced HBsAg from 3 (b) in 4 ml. 30 mM potassium phosphate buffer (pH 7.1) are added 10 mg. $\beta$-Gal-BMME in 1.6 ml. of the same buffer and, after mixing, left to react for 1 hour. The reaction is terminated by the addition of cysteine to 1 mM. After 30 minutes at 25° C., iodoacetamide is added to 5 mM and again left to react for 30 minutes. The batch is subsequently concentrated to 15 mg./ml. 3 (f) Chromatographic separation of the reaction batch.

The batch according to 3 (e) is applied to a column of 80 ml. Superose 6 prep and chromatographed at a flow rate of 5 cm./hour (buffer: 10 mM potassium phosphate buffer pH 7.5, 0.2% sucrose 0.1% azide). The fractions in the void volume are the appropriate product.

EXAMPLE 2

Determination of anti-HBs (A) Preparation of substrate buffer.
70 mmole/liter HEPES/NaOH, pH 7.0
154 mmole/liter sodium chloride
3 g./liter bovine serum albumin
5 mmole/liter chlorophenol red-$\beta$-galactoside (prepared according to Federal Republic of Germany Patent Application No. 33 45 748)
2 g./liter Tween 20 (non-ionic detergent)

(B) Preparation of reagent carriers.

(1) Reagent carrier 1.

40 $\mu$l. of a solution which contains, per liter, 100 mmole sodium phosphate (pH 7.3; 37° C.), 2 mmole magnesium chloride, 9 g. sodium chloride, 5 g. bovine serum albumin, 10 mg. HBsAg-IgG (receptor 1 solution), 250 U HBsAg-$\beta$-galactosidase conjugate (receptor 3 solution; the activity is determined with o-nitrophenyl-$\beta$-galactoside at 37° C.), is dropped on to a fleece which consists of commercially available polyester paper. Subsequently, it is dried at room temperature.

(2) Reagent carrier 2.

Sheep antibody against the Fc$\gamma$ part of mouse antibodies (receptor 2 solution) are fixed on to a cellulose fleece according to the cyanogen bromide process (see Federal Republic of Germany Patent Specification No. 1768512), whereby, per g. of fiber material, there are provided 10 $\mu$g. antibody for fixing. Non-coupled antibody is removed by washing and the fleece dried gently at room temperature.

The determination with the help of these two reagent carriers 1 and 2 takes place with the device for carrying out analytic determinations described in Federal Republic of Germany Patent Application No. A113425008.5 (cf. FIG. 1 therein).

This describes a rotor insert element for centrifugal automatic analysers comprising a formed body which has a sample application chamber which is in connection with a plurality of reagent zones, each of which contains an absorbent carrier material impregnated with a particular reagent, at least one mixing valve chamber and a measurement chamber which together constitute a sample liquid transport path which runs radially in an outward direction when the insert element is fixed to the rotor and, furthermore, at least one further chamber for the reception of a liquid and a transport path which leads from this chamber to the chamber for the carrying out of the measurement and is at least partly identical with the sample liquid transport path. The sample liquid transport path thereby passes from the sample application chamber (P) via a chamber (a) filled with absorbent material containing buffer, a chamber (c) and a first valve chamber (Vk1) arranged between the chambers (a) and (c), to a second valve chamber (Vk2) and from this, via the chamber (d) and via a receiver chamber (AK), to the measurement chamber (K). For the reception of a further liquid, there is provided a substrate chamber (PK) constructed as a pump chamber which is connected via a dosing device, consisting of the dosaging chamber (DK) and a capillary (Kap), and an overflow chamber (UK) with the second valve chamber (Vk2). FIG. 1 of Federal Republic of Germany Patent Application No. A13425008.5 shows schematically the rotor insert element used.

Reagent carrier 1 is placed on field c of the rotor insert element and reagent carrier 2 on field d. 40 $\mu$l. of sample are thereby pipetted through an opening on the upper edge directly on to the field a. 270 $\mu$l. of substrate solution are pipetted into chamber PK. By means of an appropriate centrifuging programme, in which high speeds of rotation alternate with stopping, the sample and substrate solution are then conveyed in the direction of the separation matrix and cuvette.

In the course of the programme, the receptors 1 and 3 are thereby eluted by the sample liquid from field c and the homogeneous mixture subsequently brought to reaction. On field d, the complexes formed (receptor 1: analyte: receptor 3) are bound to receptor 2.

The substrate solution is divided by the dosing chamber DK into portions, the first of which serves for washing out excess, non-complexed conjugate.

Under these conditions, the following results are obtained:

TABLE 1

| | Anti-HBsAg | | | | |
|---|---|---|---|---|---|
| U/l.[1] | 0 | 100 | 280 | 650 | 950 |
| absorbance (mE)[2] | 150 ± 5 | 260 ± 10 | 445 ± 10 | 805 ± 16 | 1111 ± 27 |

[1]Definition of the units corresponds to the standardisation of the Paul-Ehrlich Institute, Federal Republic of Germany.
[2]mE: Optical densitiy × 10$^3$ The samples were, in each case, determined 5 times. The measurements were carried out at a path length of 0.3 cm. at 576 nm against 700 nm and recalculated to a path length of d=1 cm.

EXAMPLE 3.

Microtitre plates (MTPs) are coated overnight per well with 250 $\mu$l. of a solution of immunosorptively purified receptor 2 (sheep-anti-mouse Fc$\gamma$ antibody) in a concentration of 10 $\mu$g./ml. in coating buffer (20 mM carbonate buffer; pH 9.6). Subsequently, non-specific binding points are saturated by a post-incubation for 1 hour at room temperature with 300 $\mu$l. post-coating buffer (50 mM potassium phosphate, 150 mM sodium chloride, 1% bovine serum albumin, 1 g./liter Tween 20; pH 7.5). After washing with 300 $\mu$l. washing buffer (100 mM HEPES, 150 mM sodium chloride, 2.5 g./liter sheep normal IgG, 0.5 mM magnesium L-aspartate, 2 g./liter Tween 20;pH 7.25) per well there are added 150 $\mu$l. of sample and 50 $\mu$l. of a reagent solution containing receptor 3 from Example 1 (HBsAg-$\beta$Gal conjugate, 0.1 U/ml., measurement of the activity with o-nitrophenyl-$\beta$-D-galactoside at 37° C.) and receptor 1 from Example 1 (HBsAg-mouse-IgG conjugate, 5 $\mu$g./ml.) in washing buffer, mixed by shaking and subsequently incubated for 3 hours. The wells are thereafter sucked out and washed three times with, in each case, 300 $\mu$l. of washing buffer. Thereafter, incubation is carried out for 1 hour at room temperature with 250 $\mu$l. of substrate solution (5 mM chlorophenol red-$\beta$-galactoside, 70 mM HEPES, 150 mM sodium chloride, 3 g./liter bovine serum albumin, 2 g./liter Tween 20; pH 7.3) and subsequently measured by means of a commercially available MTP measurement device at 570 nm with bichromatic correction at 630 nm.

The following Table 2 shows the results of a typical experiment (measurements in each case with n=4).

TABLE 2

| anti-HBsAg concentration (U/l.)[1] | 0 | 200 |
|---|---|---|
| mE (570 nm − 630 nm)[2] | 158 ± 19 | 912 ± 58 |

[1] Definition: see Example 2.
[2] Definition: see Example 2.

EXAMPLE 4

Coating of tubes.

Polystyrene tubes are coated for 18 to 24 hours with 4 μg./ml. avidin in a 40 mM sodium phosphate buffer at room temperature. Post-coating for the saturation of non-specific binding sites takes place with a 0.3% bovine serum albumin, 0.9% sodium chloride, 2% sucrose and 0.05% polyether glycol (pluronic L-64) containing solution.

Preparation of the hepatitis B surface antigen (HBsAg) conjugated with peroxidase:

The process is, in principle, so arranged that, by gentle reduction, SH groups in the HBsAg are liberated to which are then coupled horseradish peroxidase (POD) derivatised with maleimidohexanoyl-N-hydroxysuccinimide ester (MHS).

HBsAg is incubated for 2 hours at 25° C. at a concentration of 1.4 mg./ml. and a pH of 4.5 in the presence of 10 mM dithiothreitol (DTT) and subsequently desalinated over a Sephadex G25 fine column (Pharmacia) in 10 mM acetate buffer and gassed with argon for protection against oxidation.

POD is incubated for 1 hour at 25° C. at a concentration of 10 mg./ml. in 30 mM sodium phosphate buffer (pH 7.1) with a 25 fold molar excess of MHS. Free MHS is separated over a Sephadex G25 medium column (Pharmacia) in 10 mM potassium phosphate buffer (pH 6.1; 50 mM sodium chloride, 10 mM magnesium chloride).

The reduced HBsAg is coupled to the POD by using 3 mg. MHS-derivatised POD/mg. HBsAg at pH 7 and 25° C. After 2 hours, the reaction is stopped by the addition of cysteine to 1 mM. Finally, the SH groups are derivatised by 5 mM iodoacetamide at pH 7.5 for 1 hour at 25° C. The HBsAg-POD conjugate is then further purified in 10 mM sodium phosphate buffer (pH 7.5, 150 mM sodium chloride) via a gel filtration on AcA22 (IBF, Serva, Germany).

Preparation of biotinylated hepatitis B surface antigen:

Biotinylation is carried out with biotin-N-hydroxysuccinimide ester (E. A. Bayer and M. Wilchek, Meth. Enzymol., 34, 265-267/1980) via the amino groups in the protein:

For this purpose, HBsAg in 30 mM sodium phosphate buffer (pH 7.1) is incubated at a concentration of 1 mg./ml. for 1 hour at 25° C. with a 6 mg./ml. solution of biotin-N-hydroxysuccinimide ester in dimethyl sulphoxide. Free biotinylation reagent is separated by gel filtration on AcA 22 in 20 mM sodium phosphate buffer (pH 7.1, 150 mM sodium chloride).

Assay procedure;

The samples (200 μl serum or plasma) are incubated for 4 hours at ambient temperature in the tubes with 1000 μl of reagent. The reagent contains, as receptor $R_3$, 60 mU/ml. hepatitis B surface antigen (≙100 ng/ml) conjugated with peroxidase and, as receptor $R_1$, 150 ng./ml. biotinylated hepatitis B surface antigen in sodium phosphate buffer (pH 7.0) with 0.5% polyether glycol (Pluronic F-68), 0.2% bovine serum albumin and 0.2 M sodium tartrate.

After incubation has taken place, the tubes are washed three times with 1.5 ml. tap water and 1 ml. 2,2′-azino-di-[3-ethyl-benzthiazoline-sulphonic acid]-diammonium salt (1.9 mM) pipetted in for the substrate reaction. The absorbance is measured at 405 nm in a cuvette with 5 mm. path length and recalculated to a 1 cm. cuvette.

The results of a typical experiment are given in the following Table 3 and in FIG. 1 of the accompanying drawings:

TABLE 3

| U/l. | anti-HBs[1] | | | | | | |
|---|---|---|---|---|---|---|---|
| | 0 | 5.0 | 10 | 50 | 100 | 250 | 500 |
| absorbance (mE) | 83 | 126 | 145 | 321 | 505 | 1110 | 1934 |

[1] for definition see Example 2.

EXAMPLE 5.

Test tubes are coated with a conjugate of streptavidin and thermo-bovine serum albumin. (a) Preparation of thermo bovine serum albumin:

1 g. BSA-I is dissolved in 100 ml. 50 mMole/liter potassium phosphate buffer (pH 7.0), heated to 70° C. and maintained at this temperature for 4 hours with gentle stirring. The solution is cooled, filtered and adjusted in an ultrafiltration cell (exclusion limit: 30,000 Dalton) to a concentration of 50 mg./ml. Subsequently, it is dialysed against a 30 fold volume of double distilled water and then lyophilised. The product has a molecular weight of about 700,000.

Before coupling to streptavidin, the thermo BSA is activated. For this purpose, 68 g. thermo BSA are dissolved in 2 ml. 0.1 Mole/liter potassium phosphate (pH 7.8) and slowly mixed with a solution of 3.8 mg. S-acetylmercaptosuccinic acid anhydride (SAMBA). After a reaction period of 3 hours, it is dialysed against 2 liters 50 mMole/liter potassium phosphate (pH 6.5) at 4° C.

(b) Preparation of streptavidin coupled to thermo-BSA. Activation of streptavidin:

60 mg. Streptavidin are dissolved in 6 ml. 5 mMole/liter potassium phosphate/100 mMole/liter sodium chloride (pH 7.0) and cooled to 4° C. 6.16 mg. Maleinimidohexanoyl-N-hydroxysuccinimide ester (MHS) are dissolved in 620 μl. dioxan and stirred into the streptavidin solution. After a reaction time of 2 hours at 4° C., it is dialysed twice at 4° C. against 1 liter 50 mMole/liter potassium phosphate/100 mMole/liter sodium chloride (pH 5).

Preparation of a conjugate of streptavidin and thermo BSA:

66 mg. MHS derivated Streptavidin are dissolved in 10 ml. 50 mMole/liter potassium phosphate (pH 5.0) and 100 mMole/liter sodium chloride and 72 mg. activated thermo BSA-SAMBA in 5 ml. 50 mMole/liter potassium phosphate/100 mMole/liter sodium chloride (pH 6.5) are added thereto. After mixing, 50 μl. 1 mole/liter hydroxylamine (pH 7.0) are added thereto in order to stop the reaction. After 3 hours, the reaction product is purified via gel chromatography (Superose 6, 50 mMole/liter potassium phosphate/100 mMole/liter sodium chloride; pH 7.5). A conjugate is obtained with a molecular weight of from 1 to 5 mio.

In test tubes made of polystyrene or Luran (producer BASF) are placed 1.5 ml. of the streptavidin/thermo-BSA solution (10 μg./ml. streptavidin/thermo-BSA) and loaded overnight (about 22 hours). Thereafter, the test tubes are completely emptied and post-coated with a solution containing bovine serum albumin.

Biotinylated antigens are then prepared, as described in Example 4, with peroxidase-conjugated hepatitis B surface antigen and a assay carried out as described in Example 4. The results obtained are given in the following Table 4 and in FIG. 2 of the accompanying drawings:

TABLE 4

| U/l. | Anti-HBs[1] | | | | | |
|---|---|---|---|---|---|---|
| | 0 | 5 | 10 | 50 | 100 | 500 |
| absorbance (mE)[2] | 143 | 209 | 242 | 744 | 1500 | 5543 |

[1]definition see Example 2.
[2]definition see Example 2.

We claim:

1. Process for the determination of an antibody comprising incubating an antibody containing sample with three different reagents $R_1$, $R_2$ and $R_3$, wherein $R_1$ and $R_3$ are in liquid phase and $R_2$ is found to a solid phase and binds to $R_1$ but not $R_3$, wherein $R_1$ comprises a conjugate of (i) a substance having at least one epitope specific for a paratope of an antibody to be determined and is specifically recognized by said antibody to be determined and (ii) a first reaction component of a two part, specific binding system, $R_3$ comprises a conjugate of (i) a substance having at least one epitope which binds to the same paratope of the antibody to be determined as does $R_1$ and is specifically recognized by said antibody to be determined and (ii) a label, wherein $R_1$ and $R_3$ compete for binding to the two identical paratopes of the antibody to be determined, and $R_2$ comprises a second reaction component of said two part, specific binding system, so as to bind $R_1$, complexes of $R_1$ and antibody, and conjugates of $R_1$, antibody and $R_3$ to said solid phase, separating liquid phase from said solid phase and measuring $R_3$ bound to said solid phase as a measure of antibody in said sample.

2. Process according to claim 1, wherein, as specific binding system, there is used biotin/avidin; biotin/streptavidin; biotin/antibiotin; hapten/antihapten; an Fcγ fragment of an antibody/antibody against the Fcγ fragment; or carbohydrate/lectin.

3. Process according to claim 1, wherein the reagent $R_3$ is labelled with an enzyme or with a fluorescing, chemiluminescing or radio-active substance.

4. Process according to claim 1, wherein all three reagents are added simultaneously.

5. Process according to claim 1, wherein the reagents $R_1$ and $R_3$ are pre-incubated with the sample and subsequently incubated with $R_2$.

6. Process according to claim 1, wherein the amount of substance in $R_1$ specifically recognised by the antibody to be determined is greater than or equal to the amount of substance in $R_3$ specifically recognised by the antibody to be determined.

7. Process according to claim 6, wherein the ratio of the substance in $R_1$ specifically recognised by the antibody to be determined to the substance in $R_3$ specifically recognised by the antibody to be determined is 20 to 1:1.

8. Process according to claim 7, wherein the said ratio is from 5 to 1:1.

9. Composition useful in the determination of an antibody comprising:
  (a) a first soluble reagent $R_1$ which comprises a conjugate of (i) a substance having at least one epitope specific for a paratope of an antibody to be determined and is specifically recognized by said antibody to be determined, and (ii) a first reaction component of a two part, specific binding system;
  (b) a second soluble reagent $R_3$ which comprises a conjugate of (i) a substance having at least one epitope which binds to the same paratope of the antibody to be determined as does $R_1$ and is specifically recognized by said antibody to be determined and (ii) a label; and
  (c) a solid phase bound reagent $R_2$ which comprises a second reaction component of said two part, specific binding system wherein $R_1$ and $R_2$ are physically separated from each other.

10. Composition according to claim 9, wherein the reagent $R_2$ or the reagent $R_1$ are present impregnated on a carrier material, each physically separated from one another.

* * * * *